United States Patent
Schmidt et al.

(10) Patent No.: US 7,780,907 B2
(45) Date of Patent: Aug. 24, 2010

(54) METHOD FOR PRODUCING A DENTURE

(75) Inventors: Christian Schmidt, Bensheim (DE); Juha Kotila, Turku (FI)

(73) Assignee: Sirona Dental Systems GmbH, Bensheim (DE)

( * ) Notice: Subject to any disclaimer, the term of this patent is extended or adjusted under 35 U.S.C. 154(b) by 240 days.

(21) Appl. No.: 12/083,598

(22) PCT Filed: Oct. 17, 2006

(86) PCT No.: PCT/EP2006/067481

§ 371 (c)(1), (2), (4) Date: Apr. 15, 2008

(87) PCT Pub. No.: WO2007/045643

PCT Pub. Date: Apr. 26, 2007

(65) Prior Publication Data

US 2009/0233257 A1  Sep. 17, 2009

Related U.S. Application Data

(60) Provisional application No. 60/750,381, filed on Dec. 15, 2005.

(30) Foreign Application Priority Data

Oct. 17, 2005  (DE) .................. 10 2005 049 886

(51) Int. Cl.
*B22F 7/00* (2006.01)
*B23K 26/00* (2006.01)

(52) U.S. Cl. .............. 419/6; 264/497; 219/121.14; 219/121.64; 219/121.85

(58) Field of Classification Search ............ 419/6; 264/497; 219/121.12, 121.14, 121.16, 121.17, 219/121.61, 121.85
See application file for complete search history.

(56) References Cited

U.S. PATENT DOCUMENTS

| 5,640,667 | A | * | 6/1997 | Freitag et al. .................. 419/31 |
| 5,837,960 | A | * | 11/1998 | Lewis et al. ............ 219/121.63 |
| 2004/0031780 | A1 | | 2/2004 | Hagemeister et al. |
| 2005/0025656 | A1 | * | 2/2005 | Bhaduri et al. ................. 419/52 |
| 2005/0056350 | A1 | | 3/2005 | Dolabdjian et al. |
| 2005/0123672 | A1 | | 6/2005 | Justin et al. |
| 2005/0186538 | A1 | * | 8/2005 | Uckelmann .............. 433/201.1 |

FOREIGN PATENT DOCUMENTS

| DE | 10320085 | 2/2004 |
| WO | 03026714 | 4/2003 |

OTHER PUBLICATIONS

English Abstract of DE10320085.

* cited by examiner

*Primary Examiner*—Roy King
*Assistant Examiner*—Ngoclan T Mai
(74) *Attorney, Agent, or Firm*—Dykema Gossett PLLC

(57) ABSTRACT

The invention relates to a process for the production of a dental prosthetic item (10) by means of local sintering, in which the dental prosthetic item (10) is produced layer-wise by energy input, by means of an energy transferring beam (7), into a layer of powder (6) of a sinterable material. One or more parameters of the sintering process are modified during production such that the material (6) is regionally sintered to various degrees to produce denser material in the marginal region (14) of a sintered layer of said dental prosthetic item (10) than is produced in the inner region (15) of said sintered layer.

The invention furthermore relates to a dental prosthetic item (10) of a material subjected to local sintering, which material is sintered in a marginal region (14) of the dental prosthetic item (10) to a greater density than in an inner region (15).

8 Claims, 2 Drawing Sheets

State of the art

METHOD FOR PRODUCING A DENTURE

TECHNICAL FIELD

The invention relates to a process for the production of a dental prosthetic item by means of local sintering, the dental prosthetic item being produced layer-wise in individual powder layers of a sinterable material by energy input by means of an energy transferring beam.

DESCRIPTION OF THE RELATED ART

In the prior art, processes for the production of individual dental prosthetic items are known which make use of the principles of rapid prototyping.

Such a process, by means of which dental prosthetic items are produced from metallic materials, is direct metal laser sintering (DMLS) or selective laser melting (SLM). The material to be processed here usually exists in powder form, the material being distributed in uniform thickness on a support or in a dish.

The energy input of the laser causes a strong local temperature increase of the powder and consequent melting or sintering of the metal particles. As a result of the melting or sintering of the particles, material cohesion of the laser-exposed surfaces results. As soon as one layer has been completed, a new powder layer is applied and the next layer is exposed to laser.

In this process, 3D CAD data are always broken down into individual layers, which are customarily from 20 μm to 50 μm thick.

EP 1 358 855 A1 discloses such a process. Metallic or alternatively non-metallic products are produced by free-form laser sintering, the products being built up vertically layer-wise from pulverulent material on a substrate plate by means of a laser beam guided under data control. Between the substrate plate and the products there is provided a web having a predetermined breaking point. This process, however, suffers from the drawback that, as shown in practice, it is not applicable to all types of dental prosthetic items to be produced and that the dental prosthetic item produced in this way must be reprocessed in order to eliminate unevenness at the predetermined breaking point.

It is generally known in the prior art to veneer a dental prosthetic item with ceramics or porcelain following the production of a core or framework in order to produce an aesthetic visual effect and good compatibility with the surrounding tissue.

On account of the aforementioned problems, the invention serves the object of providing a process for the production of dental prosthetic items by means of local sintering, which makes it possible to produce a greater variety of dental prosthetic items.

SUMMARY AND OBJECTS OF THE INVENTION

This object is achieved by a process according to the invention as defined by the features of independent claim 1 and by a dental prosthetic item as defined by the features of independent claim 12.

According to the invention, a process for the production of a dental prosthetic item by means of local sintering is proposed in which the dental prosthetic item is produced layer-wise and by energy input by means of an energy transferring beam in the individual powder layers of a sinterable material. In this process, one or more parameters of the sintering process are modified during production such that the material is regionally sintered to various degrees to produce denser material in the marginal region of a sintered layer of the dental prosthetic item to be produced than in the inner region of said sintered layer.

Bridge frameworks and anatomically shaped solid crowns or solid teeth are examples of types of dental prosthetic items to which the process according to the invention is applicable. A bridge framework customarily consists of very thin-walled dental bridge pillars having wall thicknesses in the range of from 0.3 to 0.5 mm and, in comparison therewith, significantly more voluminous intermediate members and connectors. The elements to be produced thus have sub-regions with different dimensions. Broken down into individual layers, the dental bridge pillars consist to a major extent of annular regions and the intermediate members and connectors consist of solid regions.

The problem here is that the usually thin, annular dental bridge pillars cool down more rapidly following the input of energy than the intermediate members and connectors. Because of their smaller area, the annular regions absorb a smaller amount of heat than the solid-area intermediate members and connectors. Moreover, the mainly annular elements possess a relatively larger surface area for heat dissipation into the bed of powder. Owing to the temperature difference caused within the bridge framework by this cooling at different rates, thermal stresses are built up which act particularly strongly in the transition regions between the dental bridge pillars and the intermediate members and connectors. As a result, this can lead, on the one hand, to the detachment of the dental bridge pillars from the fixing elements for the construction platform (support structures) and, on the other hand, to deformation of the bridge framework. Deformed bridge frameworks of this type can no longer be used and can lead to collisions with the coating unit during the production process. Since usually a plurality of components is produced simultaneously in a single production run, the interruption of production usually causes all of the components being produced in this production run to be rendered useless.

The attempt to forestall this problem by increased binding of the dental bridge pillars to the construction platform by means of reinforced support structures led to a considerable increase in effort when reprocessing the bridge frameworks. This lowers the economics of this process considerably.

Alternatively, attempts have been made to reduce the degree of sintering. The degree of sintering in this context represents the ratio of the achieved to the theoretically possible density of the sintered material. In the case of degrees of sintering of approximately 80 to 90% of the theoretically possible density, the above problems occur far less frequently. However, proper veneering of such a porous structure is very much more difficult, since on account of the open pores in the marginal region defects such as frog's eyes, chipping, or the like can occur, which make the dental prosthetic item unusable. Using the process according to the invention, it is possible to eliminate the above problems.

Advantageously, a laser beam or an electron beam is used as the energy transferring beam. The properties of these beams have been scientifically investigated and are suitable for local heating of a powder.

Advantageously, the marginal region of the layer to be sintered is sintered to a density of more than 95% of the theoretically possible density and the inner region of the layer to be sintered is sintered to a density of from 60% to 95% of the theoretically possible density.

It is particularly advantageous if the marginal region is sintered to at least 99% of the theoretically possible density, since the dental prosthetic item then has adequate strength, on the one hand, and the number of rejects due to warping is minimized and, on the other hand, no open pores exist on account of the high degree of sintering in the marginal region, whereby fault-free veneers can be produced.

Advantageously, the marginal region is between 0.1 and 1 mm wide. A width of the marginal region of not more than 0.3 mm is particularly preferred. This ensures that very thin-walled elements having high strength are produced and nevertheless the major portion of the dental prosthetic items is sintered to a relatively low density.

Advantageously, the build-up rate, namely the product of the thickness of the layer of powder, the effective width of the beam, and the exposure rate, is greater in the inner region than in the marginal region. Sintering at regionally different intensities can thus be achieved.

Advantageously, the energy input of the beam is from 0.5 J/mm2 to 8 J/mm2. These energy inputs are achievable using conventional energy beams.

It has been found to be particularly advantageous if the build-up rate in the marginal region is from 1 mm3/s to 2.3 mm3/s and the energy input of the beam per unit area is from 1.3 J/mm2 to 8 J/mm2. Dental prosthetic items of high quality can be produced in this way.

Advantageously, the build-up rate in the inner region is between 2.3 mm3/s and 5 mm3/s and the energy input of the beam is between 0.5 J/mm2 and 1.8 J/mm2.

It is particularly advantageous if the tensile strength and flexural strength of the marginal region is greater than 1.1 times the tensile strength and flexural strength of the inner region. Adequate dimensional stability is thus ensured by the more rigid marginal region.

It is of particular advantage if the material used is a metal. Metals can be easily processed and have good mechanical properties for use as bridging members or other dental restorations, e.g. high tensile or flexural strength or a high modulus of elasticity.

Advantageously, the dental prosthetic item is produced by the process according to the invention.

BRIEF DESCRIPTION OF THE DRAWINGS

The process according to the invention is described below with reference to the aid of the drawings, in which:

FIG. 1 shows a well known laser sintering unit 1 for carrying out the process according to the invention.

Figure 1:
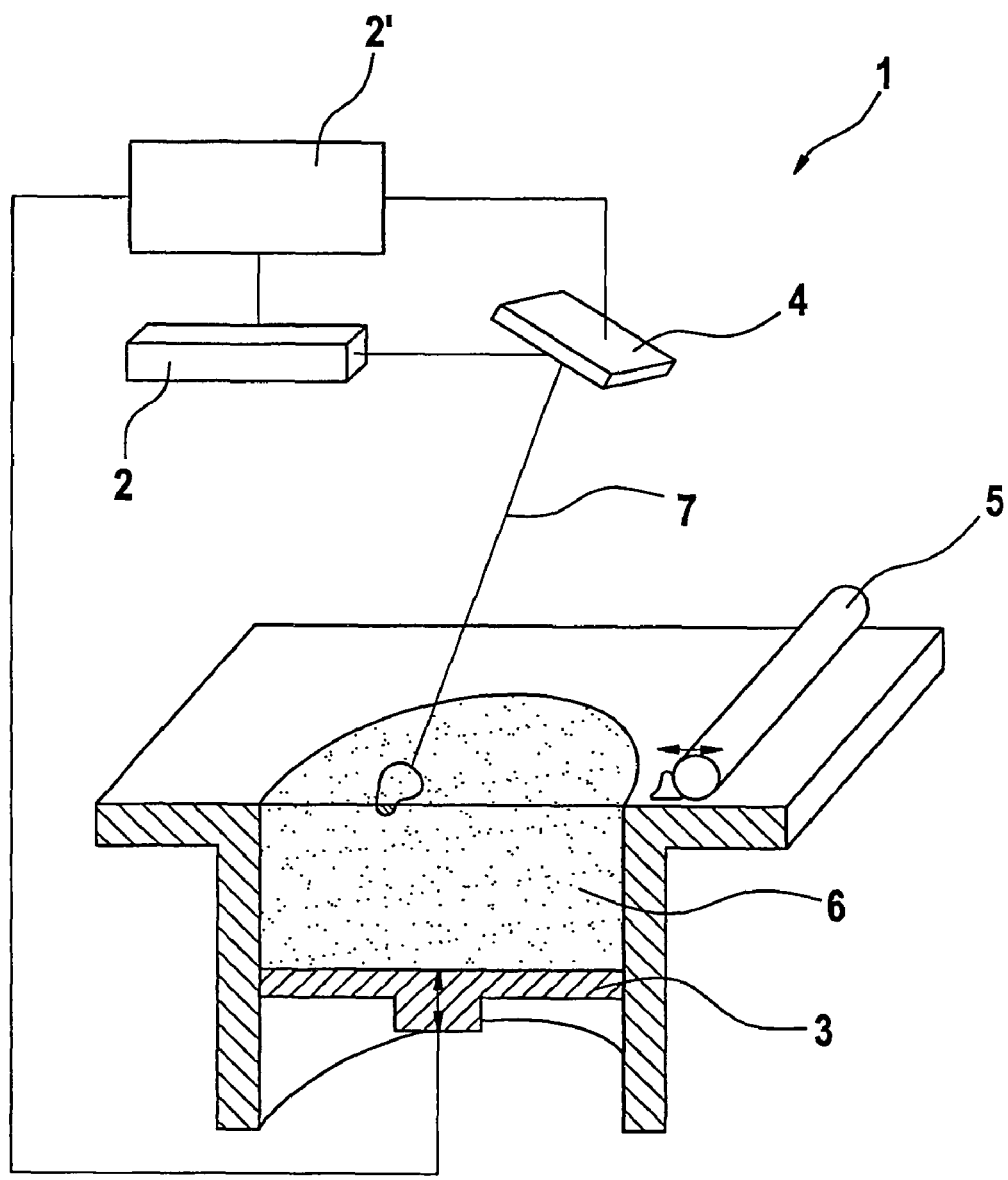
FIG. 1 shows a laser sintering unit.

A laser sintering unit 1 comprises a laser 2, which is controlled by a control unit 2', a vertically adjustable support platform 3, a deflecting mirror 4 for guiding a laser beam 7 in the plane of the surface of the powder 6, and a coater unit 5.

Control unit 2' is used for controlling laser 2, support platform 3, deflecting mirror 4, and coater unit 5. The control unit 2' can calculate layer data for layers of the dental prosthetic item to be produced from 3D volume data of the design.

The intensity of laser 2 is controlled by control unit 2'.

Other possibilities of varying the position of laser beam 7 on the surface of powder 6 are likewise conceivable. For example, this can be achieved by means of a swinging laser and/or a traveling laser or a scanning unit. It is only essential to ensure that laser beam 7 reaches every point on the surface of the bed of powder 6 which lies within the surface of the dental prosthetic item to be produced.

Coater unit 5 is used for applying a new powder layer after the production of a layer to be sintered. Powder 6 is exposed to laser beam 7, which is produced by laser 2.

Figure 2:
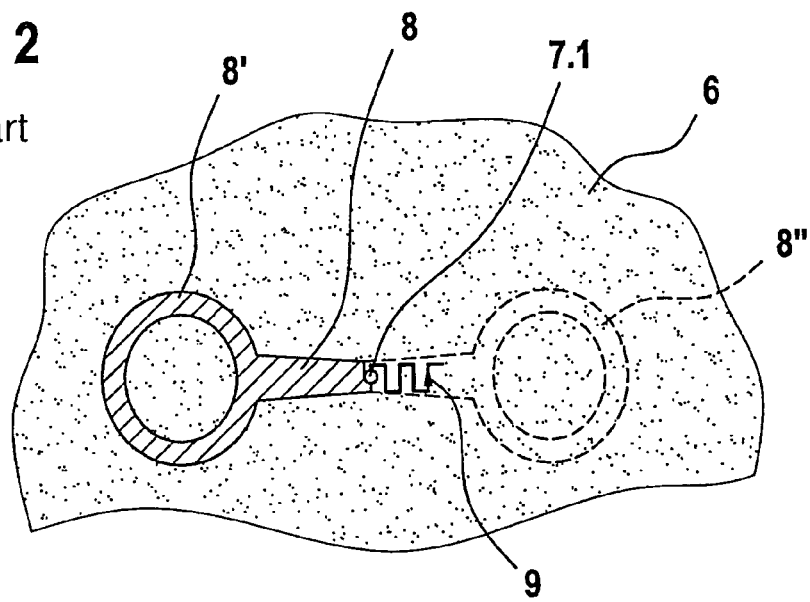
FIG. 2 illustrates the production of a dental bridge framework as in the prior art.

FIG. 2 illustrates the production of a dental bridge framework 8 by laser sintering as known in the prior art.

Laser beam 7 is focused onto the surface of powder 6. The contours of the desired component layer 8' of bridge framework 8 are calculated by a computer or the control unit. The CAD 3D model is broken down into layers for this purpose. From these layers, path data for the relative movement between laser 7 and support platform 3 are calculated. Laser beam 7 travels along path 9 sketched by way of example on paths the spacing of which is less than the width of the focused part 7.1 of laser beam 7. The still unfinished part 8" of component layer 8' is indicated by dashed lines.

Following completion of the laser-exposure of component layer 8', the application of a new layer of powder takes place in order to expose the next component layer.

Figure 3:
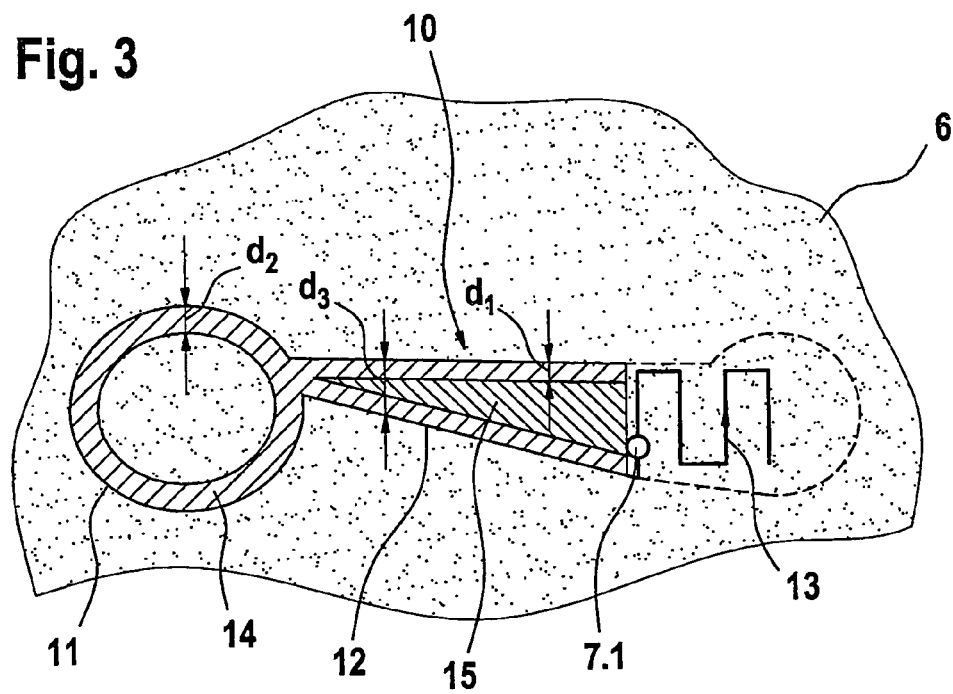
FIG. 3 illustrates the production of a dental bridge framework according to the invention.

According to the invention, another process for the production of a dental prosthetic item is proposed, this being explained below with reference to FIG. 3.

Bridge framework 10 to be produced by means of laser sintering consists of a dental bridge pillar 11 and a connector 12. The focused part 7.1 of laser beam 7 is guided, in a similar way to that shown in FIG. 2, along paths over the bed of powder 6.

Unlike the process illustrated in FIG. 2, the energy input per unit area in this process varies regionally.

In the marginal region 14 of bridge framework 10, the process parameters are chosen such that the degree of sintering of the material produces at least 99% of the theoretically possible density. The energy input per unit area, that is, the laser power for the effective width times the exposure rate, in marginal region 14 is approximately 2 J/mm$^2$ with a build-up rate of 2.08 mm$^3$/s.

In the inner region 15 of bridge framework 10, the build-up rate is increased beyond that achieved in marginal region 14 and the laser power is reduced, whereby on the whole the energy input per unit area and thus also the degree of sintering also drops. The build-up rate in inner region 15 is 2.4 mm3/s and the laser power is 3500 W/mm2. The degree of sintering producing 90% of the theoretically possible density is high enough to fulfill the demands concerning the loading capacity, in spite of the residual porosity still existing. Degrees of sintering producing more than 80% of the theoretically possible density have proven to be useful when suitable materials are chosen.

The width d1 of marginal region 14 is ideally 0.3 mm. In positions in which the width of bridge framework 10 is less than twice the width, i.e. 2×0.3 mm, for example at dental bridge pillars 11 (the wall density d2 of dental bridge pillar 11 is on average approximately 0.4-0.5 mm), the section consists only of densely sintered material.

Only when the width of the surface elements of bridge framework 10 is greater than 2×d1, as, for example, in the 0.8 mm wide position d3, does an inner region 15 having a lower degree of sintering exist. Dental bridge pillars 11 and also the transition region leading to the connectors are thus usually solidly sintered and highly loadable.

Preferred materials for the application of the process according to the invention are cobalt-chromium alloys having contents of tungsten and molybdenum. Preferably, the proportions by weight of the alloy are Co>60%; Cr>25%; W>5%; Mo>5%. High gold-containing gold alloys and titanium alloys are also suitable.

The invention claimed is:

1. A process for the production of a dental prosthetic item (10) by means of local sintering, in which said dental prosthetic item (10) is produced layer-wise in the individual layers of powder of a sinterable material (6) by energy input by means of an energy transferring beam (7), wherein one or more parameters of the sintering process are modified during production such that the material (6) is regionally sintered to various degrees to produce denser material in the marginal region (14) of a sintered layer of said dental prosthetic item (10) than is produced in the inner region (15) of said sintered layer, said marginal area (14) of the layer to be sintered being sintered to a density of more than 95% of the theoretically possible density and the inner region (15) of the layer to be sintered is sintered to a density of from 80% to 95% of the theoretically possible density, with the build-up rate in the marginal region (14) being from 1 mm$^3$/s to 2.3 mm$^3$/s and the energy input of the beam (7) per unit area being from 1.3 J/mm$^2$ to 8 J/mm$^2$, while the build-up rate in the inner region (15) is from 2.3 mm$^3$/s to 5 mm$^3$/s and the energy input of the beam (7) is from 0.5 J/mm$^2$ to 1.8 J/mm$^2$.

2. The process as defined in claim 1, wherein the energy transferring beam is a laser beam (7) or a beam of electrons.

3. The process as defined in claim 1, wherein the dental prosthetic item (10) is a bridge framework or an anatomically shaped solid crown or an anatomically shaped solid tooth.

4. The process as defined in claim 1, wherein said marginal area (14) is from 0.1 to 1 mm wide.

5. The process as defined in claim 1, wherein the build-up rate, namely the product of the thickness of the layer of powder, the path width of the ray (7) and the exposure rate, is greater in the inner region (15) than in the marginal region (14).

6. The process as defined in claim 1, wherein the energy input of the beam (7) is from 0.5 J/mm$^2$ to 8 J/mm$^2$.

7. The process as defined in claim 1, wherein the tensile strength and flexural strength of the marginal region (14) is greater than 1.1 times the tensile strength and flexural strength of the inner region (15).

8. The process as defined in claim 1, wherein the material (6) is a metal.

* * * * *